United States Patent
Kim (10) Patent No.: US 11,564,826 B2
(45) Date of Patent: Jan. 31, 2023

(54) MALE PENIS JELQ EXERCISE DEVICE

(71) Applicant: Gwang-Suk Kim, Gwangju (KR)

(72) Inventor: Gwang-Suk Kim, Gwangju (KR)

( * ) Notice: Subject to any disclaimer, the term of this patent is extended or adjusted under 35 U.S.C. 154(b) by 301 days.

(21) Appl. No.: 16/484,797

(22) PCT Filed: Feb. 26, 2018

(86) PCT No.: PCT/KR2018/002330
§ 371 (c)(1),
(2) Date: Aug. 8, 2019

(87) PCT Pub. No.: WO2018/155978
PCT Pub. Date: Aug. 30, 2018

(65) Prior Publication Data
US 2020/0038225 A1    Feb. 6, 2020

(30) Foreign Application Priority Data
Feb. 27, 2017 (KR) .................. 10-2017-0025388

(51) Int. Cl.
*A61F 5/41* (2006.01)
*A61H 1/02* (2006.01)

(52) U.S. Cl.
CPC ............ *A61F 5/41* (2013.01); *A61H 1/0218* (2013.01); *A61F 2005/411* (2013.01);
(Continued)

(58) Field of Classification Search
CPC ... A61F 5/41; A61F 2005/411; A61H 1/0218; A61H 2205/087
(Continued)

(56) References Cited

U.S. PATENT DOCUMENTS 4,429,689 A * 2/1984 Yanong .................... A61F 5/41
600/39
7,276,040 B2 10/2007 Gomez-De-Diego
(Continued)

FOREIGN PATENT DOCUMENTS

CA    2849222 A1    10/2015
CN    102202615 A    9/2011
(Continued)

OTHER PUBLICATIONS

KR Grant of Patent dated Feb. 22, 2018 as received in Application No. 10-2017-0025388.

*Primary Examiner* — Samuel G Gilbert
(74) *Attorney, Agent, or Firm* — Maschoff Brennan (57) ABSTRACT

Disclosed is a male penis jelq exercise device of the present invention. A main body part which is furnished with a traction part, having a hollow portion into which the penis is to be inserted, for holding and pulling a side adjacent to the glans, and an elastic traction part which surrounds the penis and extends from the traction part toward the body-side of the penis shaft to come into contact with the body, thereby providing traction force for moving the glans forward; and a traction unit which is furnished with a fastening part coupled to the leg or body, a coupling part hung from the traction part of the main body part and formed as a loop, and an elastic band part connecting the coupling part and the fastening part and providing elastic force for pulling the penis.

4 Claims, 10 Drawing Sheets

(52) U.S. Cl.
CPC .............. *A61H 2201/0119* (2013.01); *A61H 2203/0406* (2013.01); *A61H 2205/087* (2013.01)

(58) Field of Classification Search
USPC ..................................................... 600/38–41
See application file for complete search history.

(56) References Cited

U.S. PATENT DOCUMENTS

| | | | |
|---|---|---|---|
| 7,828,718 B2 | 11/2010 | Ono | |
| 8,075,473 B2 | 12/2011 | Rudi | |
| 9,826,782 B2 | 11/2017 | Okada | |
| 2006/0243283 A1* | 11/2006 | Montgomery | A61F 5/41 128/844 |
| 2009/0287041 A1* | 11/2009 | Adams | A61F 5/41 600/38 |
| 2009/0318754 A1 | 12/2009 | Ettmer | |
| 2010/0016656 A1 | 1/2010 | Rudi | |
| 2010/0081870 A1 | 4/2010 | Lehmann | |
| 2012/0220820 A1 | 8/2012 | Gomez De Diego | |
| 2014/0206932 A1* | 7/2014 | Tait | A61B 90/00 600/38 |
| 2016/0015594 A1 | 1/2016 | Mercado | |
| 2016/0151226 A1* | 6/2016 | Leddy | A61F 5/41 600/38 |
| 2016/0189695 A1 | 6/2016 | Mynatt | |

FOREIGN PATENT DOCUMENTS

| | | |
|---|---|---|
| CN | 103536380 A | 1/2014 |
| DE | 166188 C | 12/1905 |
| EP | 2 032 095 B1 | 1/2012 |
| EP | 2 491 897 A1 | 8/2012 |
| EP | 2 099 396 B1 | 6/2013 |
| JP | S6014811 A | 1/1985 |
| JP | 2001269361 A | 10/2001 |
| JP | 2006112530 A | 4/2006 |
| JP | 2009-240461 A | 10/2009 |
| JP | 4656591 B2 | 3/2011 |
| JP | 2012507386 A | 3/2012 |
| KR | 10-2011-0010714 A | 2/2011 |
| KR | 20-2013-0007398 U | 12/2013 |
| KR | 10-2016-0123896 A | 10/2016 |
| WO | 2014116752 A1 | 7/2014 |

* cited by examiner

MALE PENIS JELQ EXERCISE DEVICE

TECHNICAL FIELD

The present invention relates to a male jelq exercise device, and more particularly to a male jelq exercise device which can increase the pulling force of a penis, can be easily coupled to or separated from the penis, and can provide a consistent tensile force or a pulling force.

BACKGROUND ART

In general, a penis is both a sexual organ of a man and a circumferential erectile tissue containing a portion of a urethra, and has a pair of cavernous bodies of the penis forming the outside thereof, one cavernous body of the urethra in the interior thereof, and a glans at a distal end thereof.

Such a penis can achieve the sexual function as a large amount of blood is introduced into the penis by psychological and physical stimuli and the cavernous bodies of the penis are expanded. However, when there is a problem in sexual lives due to the improper blood circulation and length of the penis, erectile dysfunction, and a sexual function disorder cause that hinders smooth expansion of the penis even in the case of psychological and physical stimuli, a normal sexual function can be maintained through internal medicine or surgical operations of the urology.

Further, it is preferable that the shape of the penis is formed in the lengthwise direction thereof, but in the case of a curved penis due to the curving or bending of the penis caused by a wrong sexual life or a wrong posture, a correction device that may correct the shape of the penis rather than a surgical operation is necessary.

However, a product for correction of a penis is not circulated yet. Moreover, the small size of a penis as well as the curved penis may hinder a normal sexual life, causing a psychological contraction, and men are expanding the size of their penises through an auxiliary device or a surgical operation, which cause high costs.

A conventional correction device for treating curving of a penis is disclosed in U.S. Pat. No. 7,276,040 (published on Oct. 2, 2007). The correction device is a device that is provided with fitting members on an end and an opposite end of a penis of a man to support the penis at a fixed angle to correct deflection of the penis by widening the opposite fitting members. The device is a device for only correcting the curved penis, and has no configuration or effect for overcoming a small size of the penis or premature ejaculation.

Further, German Patent No. DE166188 mentions a device for straightening a urethra, curving the penis, and treating a contractible stimulus that causes pains during urination. However, the above-described conventional technology is not provided with a device for overcoming the small size of a penis but simply precisely support the penis according to the size and length of the penis, and is used for the purpose of treatment for the curving of the penis to remove the pains during urination and has a problem of causing inconvenience to the user because it has no correction function before and after the erection of the penis.

The conventional technology has an inconvenience of always wearing two extension members, a glans accommodating member supported by the two extension members, and a base member that supports the extension members, and the everyday life of the user is inconvenient because the location and the direction of the penis are not fixed after the entire configurations are mounted.

It is essential to consistently pull the penis within a predetermined period of time to treat the small size of the glans, the extension and the curving of the penis, and it is not easy to fix or hold the glans for pulling when the size of the glans is small. In particular, because the conventional glans device for pulling cannot fix the entire glans with a uniform holding force, the penis having a small glans may be withdrawn and it is difficult to exercise in a mounting state.

A male sexual function improving traction device is disclosed in Korean Patent Application Publication No. 2016-0123896, and a penis maintaining/fixing method is disclosed in Korean Patent Application Publication No. 2011-0010714.

A penis reinforcing device is disclosed in Korean Utility Model No. 2013-0007398. The disclosed penis reinforcing device has a structure in which a ring forming member is installed in a weight and is mounted on an end of a penis.

However, according to the technical configuration, the action of the user is unnatural because the weight is fixed to the penis, and pains are caused in a mounting part during mounting of the ring forming member because the ring forming member installed in the weight is directly fixed.

According to the correction device for traction of a penis, the blood cannot circulate smoothly because a portion of the penis, which is adjacent to the glans of the penis is bound, fastened and supported, and severe pains are caused because a holding force cannot be adjusted (changed) when the penis is erected in the mounting state. Further, if the binding portion is prolonged during the erection, the penis is withdrawn from the binding portion when the penis is contracted. When the glans portion is bound not to be withdrawn, pains are caused in the binding portion.

DETAILED DESCRIPTION OF THE INVENTION

Technical Problem

A technical problem to be solved by the present invention is to provide a male penis jelq exercise device which can prevent an end of a penis from being severely fastened regardless of the thickness of the penis when the penis is pulled, can prolong the penis by using a consistent pulling force or tensile force, and can prevent damage to the penis or pains by changing a holding force when the penis is erected or contracted.

Another technical problem to be solved by the present invention is to provide a male penis jelq exercise device which can prevent a testicle from being pulled due to a tensile force or pulling force, can prevent pains or hypothermal bleeding due to a pulling force, can expedite secretion of male hormone by consistently messaging the penis, and can maximize the expansion effect of the penis.

Technical Solution

In accordance with an aspect of the present invention, there is provided a male penis jelq exercise device including a main body including a traction part having a hollow portion fitted with the penis, and configured to hold and pull a side thereof, which is adjacent to the glans, and an elastic traction part extending from the traction part to the body side of the penis shaft to contact the human body while surrounding the penis, and configured to provide a traction force for moving the glans forwards, and a traction unit including a fastening part coupled to a leg or the human body, a coupling part caught by the traction part of the main body and formed as a loop, and an elastic band part connecting the coupling part and the fastening part and configured to provide an elastic force for pulling the penis.

According to the present invention, the traction part may include a band, of which a thickness on at least one lengthwise side is larger than a thickness of the inner side thereof such that the band provides a holding force by using a winding force, and an annular coupling/insertion groove, to which the coupling part is coupled, is formed by bending an end of the main body rearwards such that the end of the main body surrounds the band.

Further, the elastic traction part may further include an elastic core member for elastically deforming the elastic traction part in a lengthwise direction thereof.

A testicle ring configured to separate the testicle from the groin while surrounding the testicle and provide a pressure to the testicle is further provided at a rear end of the elastic traction part corresponding to a rear end of the main body. The coupling part is formed at an end of the elastic band I the form of a loop.

In accordance with another aspect of the present invention, there is provided a male penis jelq exercise device including a main body having a traction part having a hollow portion fitted with the penis, and for holding a side of the penis, which is adjacent to the glans, and extending the penis, and at least one elastic support ring fitted with the penis between the main body and the penis shaft and configured to elastically bias the penis in the extension direction.

Advantageous Effects of the Invention

The male penis jelq exercise device of the present invention can provide a consistent variable pulling force to a penis by using a motion of a human body. In particular, because the coupling part for pulling is coupled to the band having the thick opposite lengthwise sides while the band is wound on an end of the penis to provide a pulling force to the penis, pains due to the pulling of the penis can be reduced.

Further, a holding force can be adjusted by using a winding tension of the band and a flexible force of the main body including silicon because the band is formed of an elastic force, and the penis can be prevented from being separated from the pulling force by varying the holding force due to the flexibility during the erection and contraction of the penis. In particular, the user can make water even in the mounting state because the elastic force according to the holding of the pulling part of the penis can vary.

In addition, according to the male penis jelq exercise device of the present invention, an end of the penis can be pushed to the front side to provide a tensile force to the penis by installing the plurality of rings in the penis between the pulling part and the human body, and the structure is relatively simple because a separate device for pulling is not necessary. Further, the degree of freedom of the activity of the human body can be increased after the mounting.

BEST MODE

A male penis jelq exercise device 10 according to the present invention is adapted to consistently provide a tensile force or a pulling force to a penis to correct the penis, and the embodiments are illustrated in FIGS. 1 to 7.

Referring to the drawings, the male penis jelq exercise device 10 according to the present invention is adapted to provide a consistent pulling force and a variable pulling force to the penis, and includes a main body 20 having a hollow portion 21 fitted with the penis 100, and a traction unit 50 configured to consistently provide a pulling force to a traction part 22 formed at an end of the main body 20.

The main body 20 is formed of silicon that is a flexible synthetic resin, and the present invention is not limited thereto and may be formed of a material that has a unique elastic force and is flexible, that is, natural rubber, expandable rubber, or the like.

The main body 20 has a hollow part 21 fitted with the penis, and includes a traction part 22 coupled to a coupling part 51 of the traction unit 50, which will be described below, at an end thereof, and an elastic traction part 25 extending from the traction part 22 to the rear side, that is, toward the shaft of the penis 100. The elastic traction part 25 and the traction part 22 of the main body 20 have diameters which gradually decrease as they go from the rear end of the elastic traction part 25 toward the front end of the traction part 22, and it is preferable that the inner peripheral surface of the elastic traction part 25 does not contact the outer peripheral surface of the penis. Further, the thickness of the traction part 25 is smaller than the thickness of the elastic traction part 25.

The traction part 22 is located on the front side of the main body 21, and includes a band winding part 22c, on which a band 30, which will be described below, is wound, at an end of the main body 21, and a bending part 22a which is bent to the rear side, on the outside. The bending part 22a is located on the bent inner side, that is, between the outer peripheral surface of the main body 22 and the inner peripheral surface of the bending part 22a, and forms a coupling/insertion groove 22b by the band 30, which will be described below.

Figure 1:
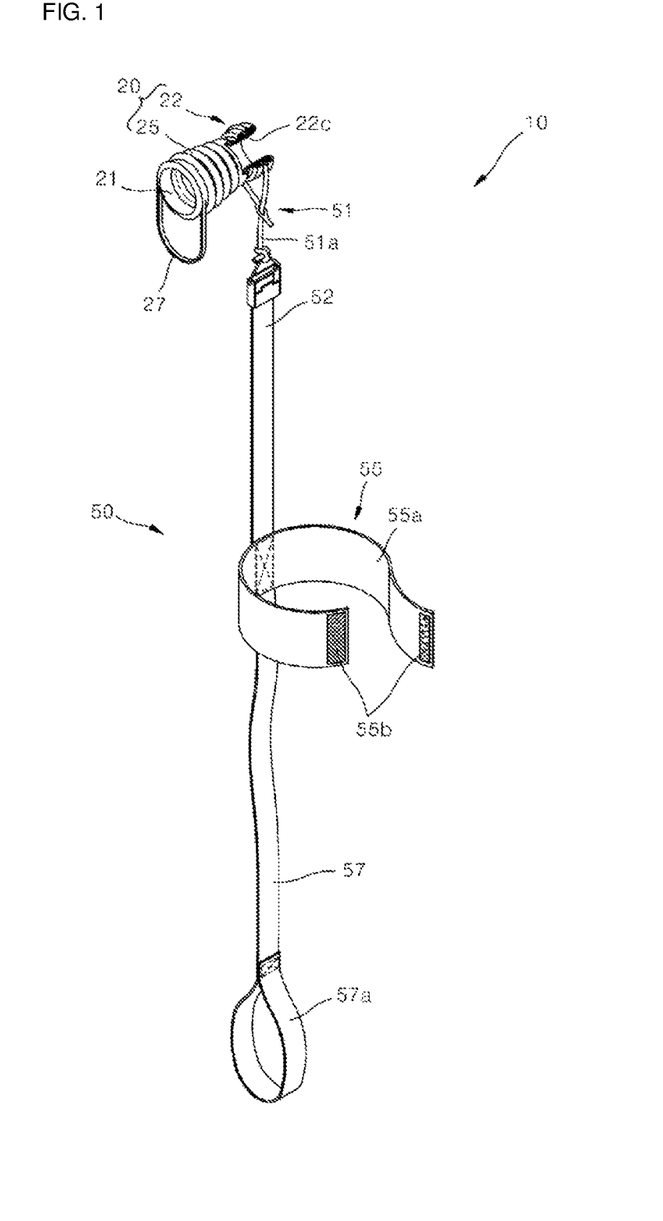
FIG. 1 is a perspective view illustrating an embodiment of a male penis jelq exercise device according to the present invention.
Figure 4:
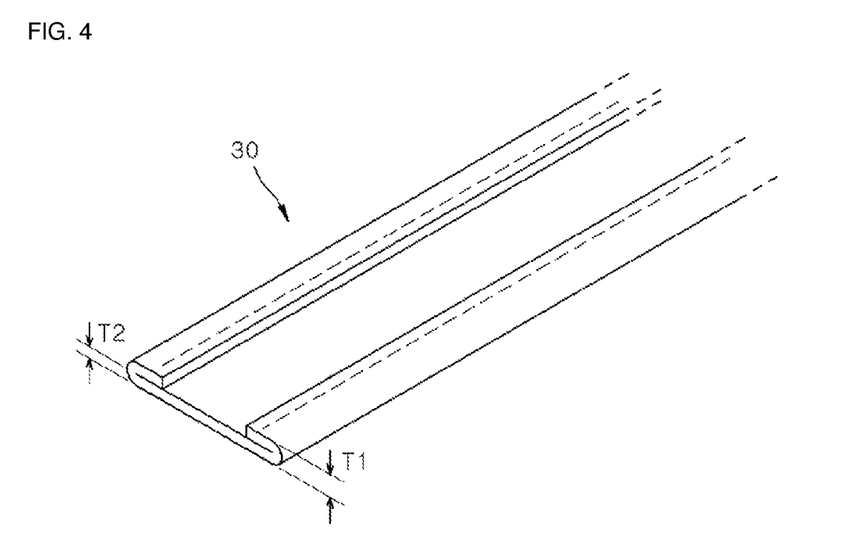
FIGS. 4 and 5 are perspective views illustrating extracted ones of the embodiments of the band illustrated in FIG. 1.
Figure 5:
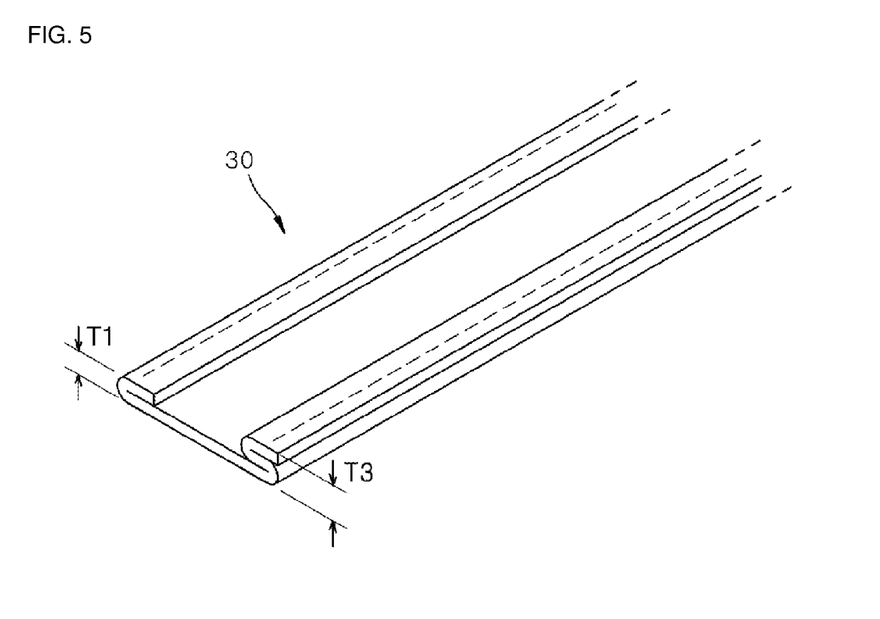
Figure 6:
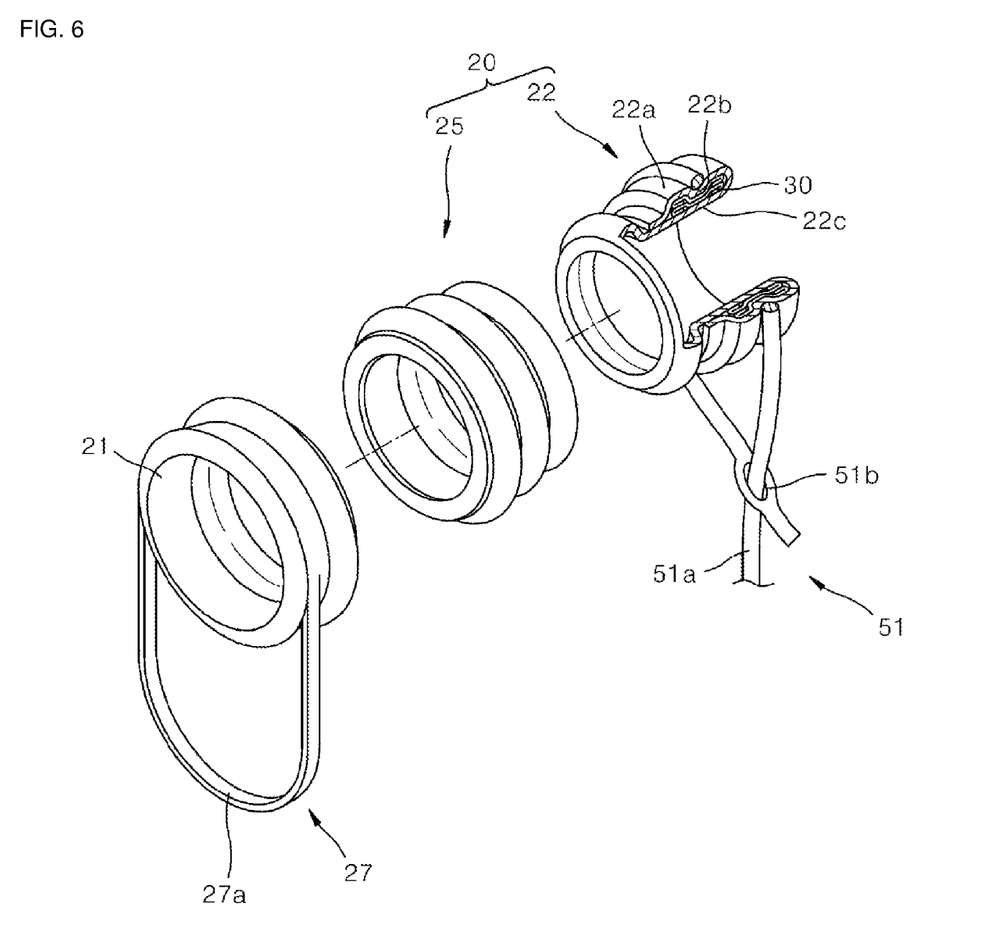
FIG. 6 is a perspective view illustrating another embodiment of the male penis extending and correcting device according to the present invention.

This band, as illustrated in FIGS. 1, 4, and 5, is formed of an elastic resin, a rubber, or elastic cloth, and may adjust the holding force of the penis by the traction part 22, by adjusting the winding force for the penis. The band 30 has a strip shape having a predetermined length, and the thickness T1 on opposite lengthwise sides or an opposite side thereof is larger than the thickness T2 of the inner side thereof. However, the present invention is not limited thereto, and as illustrated in FIG. 5, the thickness T3 of the periphery of the front side thereof may be thicker than the thickness T1 of the periphery of the rear side thereof.

The thickness difference may be achieved through folding in the lengthwise direction and sewing. Further, the width of the band 30 is smaller than the width of the bending part 22a formed by bending an end of the main body 20. The band 30 wound between the bending part 22a and the main body 20 forms the coupling/insertion groove 22b on the outer peripheral surface of the bending part 22a. That is, as the band 30, of which the opposite ends are relatively thick is wound, the opposite sides of the wound bend 30 overlap each other so that the periphery thereof may be higher than the central portion thereof. The formation of the coupling/insertion groove 22b is not limited to the above-described embodiment, and the outer peripheral surface of the main body 20 is formed relatively thick and the coupling/insertion groove 22b recessed by a predetermined length may be formed on the outer peripheral surface thereof.

Figure 7:
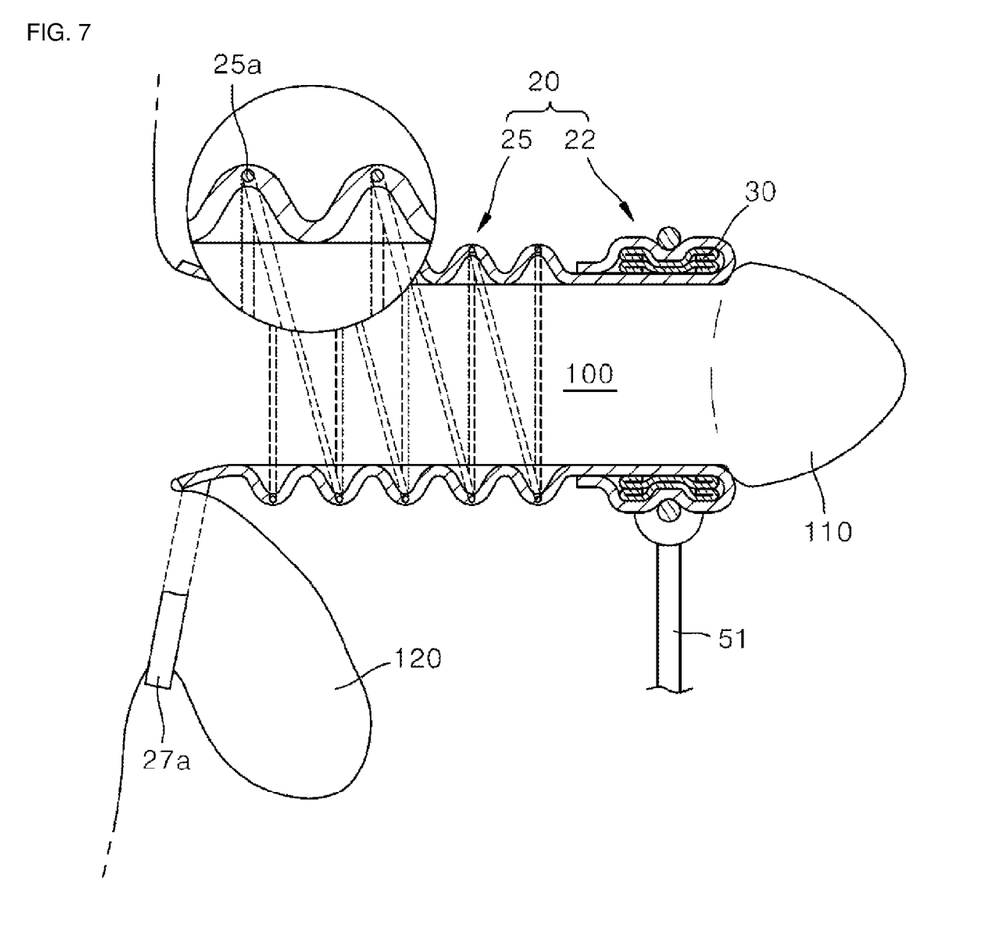
FIG. 7 is a cross-sectional view illustrating another embodiment of a male penis extending and correcting device according to the present invention.

Further, the elastic traction part 25 constituting the main body 20 extends from the traction part 22 toward the rear end of the main body 20, and has a bellows structure that is prolonged in the lengthwise direction such that a pulling force may be provided to the glans of the penis 100 by moving the glans to the front side when the penis 100 is inserted. That is, the bellows structure may have spiral or waveform convexo-concaves in which the inner peripheral surface and the outer peripheral surface of the elastic traction part 25 of the main body 20 are continuous in the lengthwise direction thereof. The elastic traction part 25 is not limited to the embodiment, and may have a structure that may be prolonged by the unique elastic force of the material. To achieve this, as illustrated in FIG. 7, an elastic core member 25a having a relatively small diameter may be inserted into the interior of the bellows part. The elastic core member 25a that provides an elastic force for prolonging of the elastic traction part 25 may be a coil spring, and the present invention is not limited thereto but may be an elastic piece of a bellows structure. The elastic traction part 25 may provide an elastic force as the thickness thereof becomes larger as it goes from the traction part to the rear side.

Figure 2:
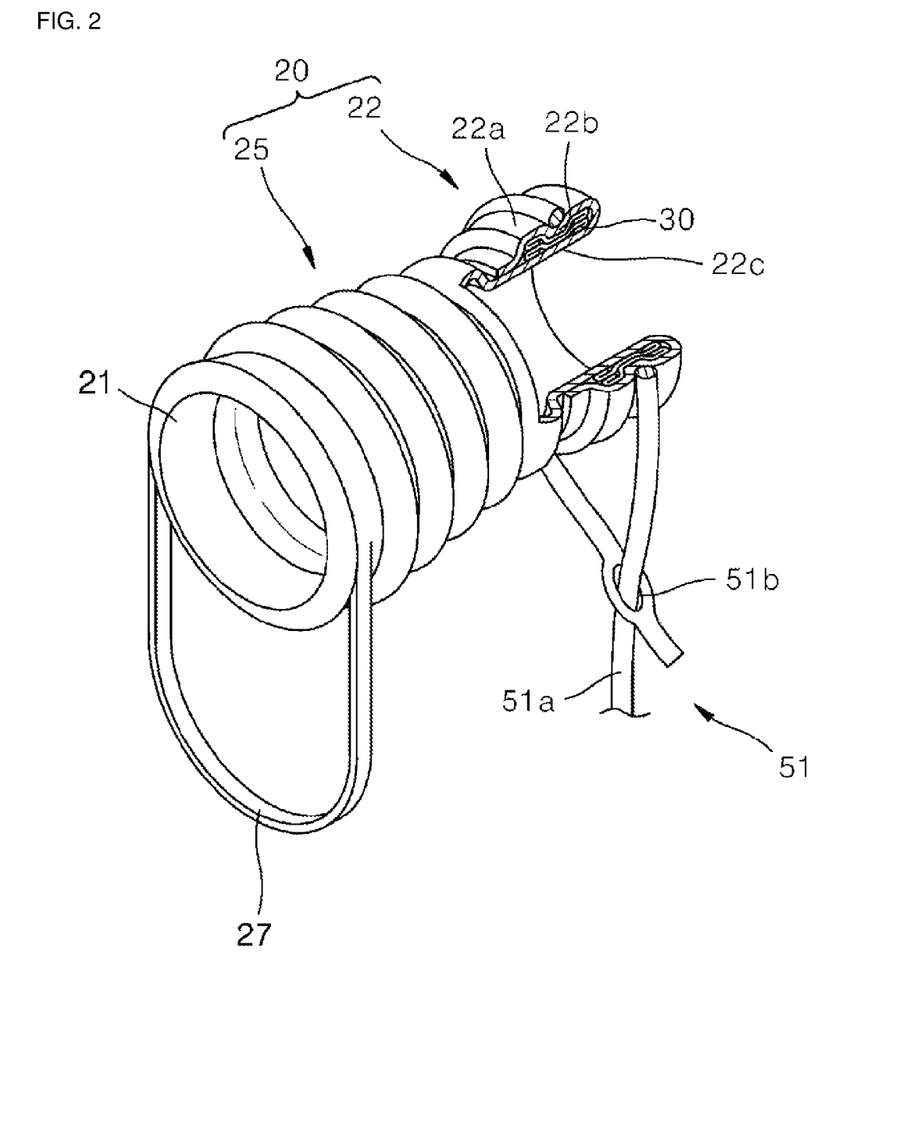
FIG. 2 is an enlarged partially cutaway perspective view of a male penis extending and correcting device according to the present invention.
Figure 3:
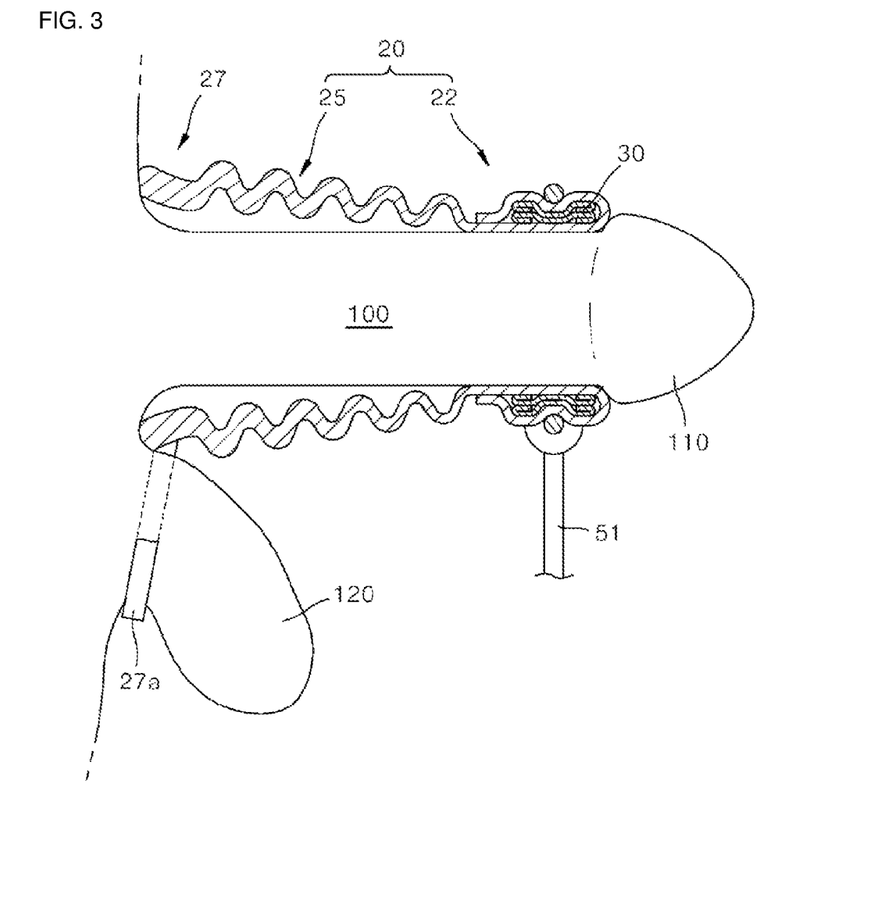
FIG. 3 is a cross-sectional view of the male penis extending and correcting device.

As illustrated in FIGS. 1 and 2, a testicle ring 27, into which the testicle 110 is inserted, may be installed at a rear end of the main body 20, and the testicle ring 27 separates the testicle from the groin and prevents the main body 20 from being separated from the penis as well. As described above, the testicle ring 27 may be formed integrally with the main body, and may be coupled to or separated from the main body 20.

As illustrated in FIG. 7, the section of the main body 20, in which the traction part 22, the elastic traction part 25, and a fixing ring 27 are installed, may be separated or coupled. The separated main body 20 may be selectively used according to the necessity of the user.

The traction unit 50 is adapted to consistently pull the traction part 22 of the main body 20, into which the penis 100 is inserted, with an uneven pulling force, and includes a coupling part 51 coupled to the traction part 22, a fastening part 55 coupled to the leg or the human body, and an elastic band part 52 connecting the coupling part 51 caught by the traction part 22 of the main body and the fastening part and configured to provide an elastic force for pulling the penis.

As illustrated in FIGS. 1 and 2, the traction unit 50 and the coupling part 51 have loop shapes, and a ring part 51b is formed at an end of a coupling strand 51a, and an opposite end of the coupling part 51 is inserted the ring part 51b to form a ring and is coupled to the flexible elastic band part 52. The coupling strand 51a does not necessarily have to have an elastic force.

The fastening part 55 is coupled to the elastic band part 52, and includes a fastening main body 55a installed along the outer peripheral surface of the thigh to be fixed to the thigh that is adjacent to the knee, and a fastening body coupling part 55b that couples ends of the fastening main body 55a. The fastening body coupling part 55b may be a Velcro tape that connects opposite ends of the fastening main body 55a, and the present invention is not limited thereto.

Although it has been described as an example that the fastening part 55 is fixed to the leg, the present invention is not limited thereto and may be mounted on the neck or the waist.

Further, the coupling unit 50 may further include an auxiliary elastic band part 57 connected to the fastening part 55 and coupled to the foot. An auxiliary ring part 57a, into which the foot is inserted, may be formed at an end of the auxiliary elastic band part 57.

Figure 8:
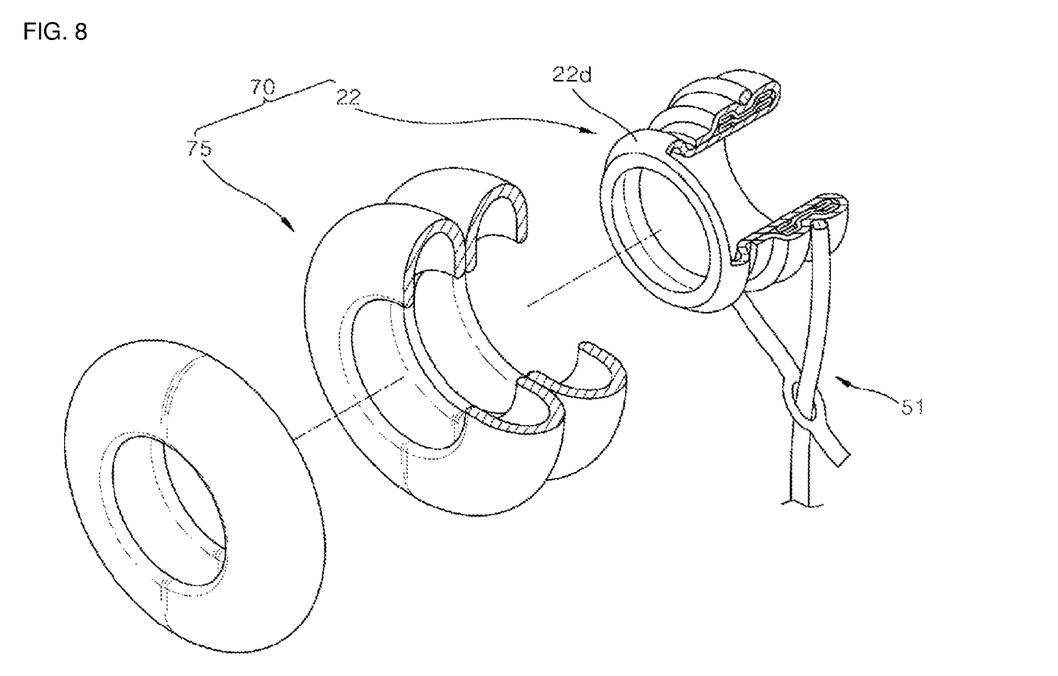
FIGS. 8 and 9 are perspective views illustrating another embodiment the male penis extending and correcting device according to the present invention.
Figure 9:
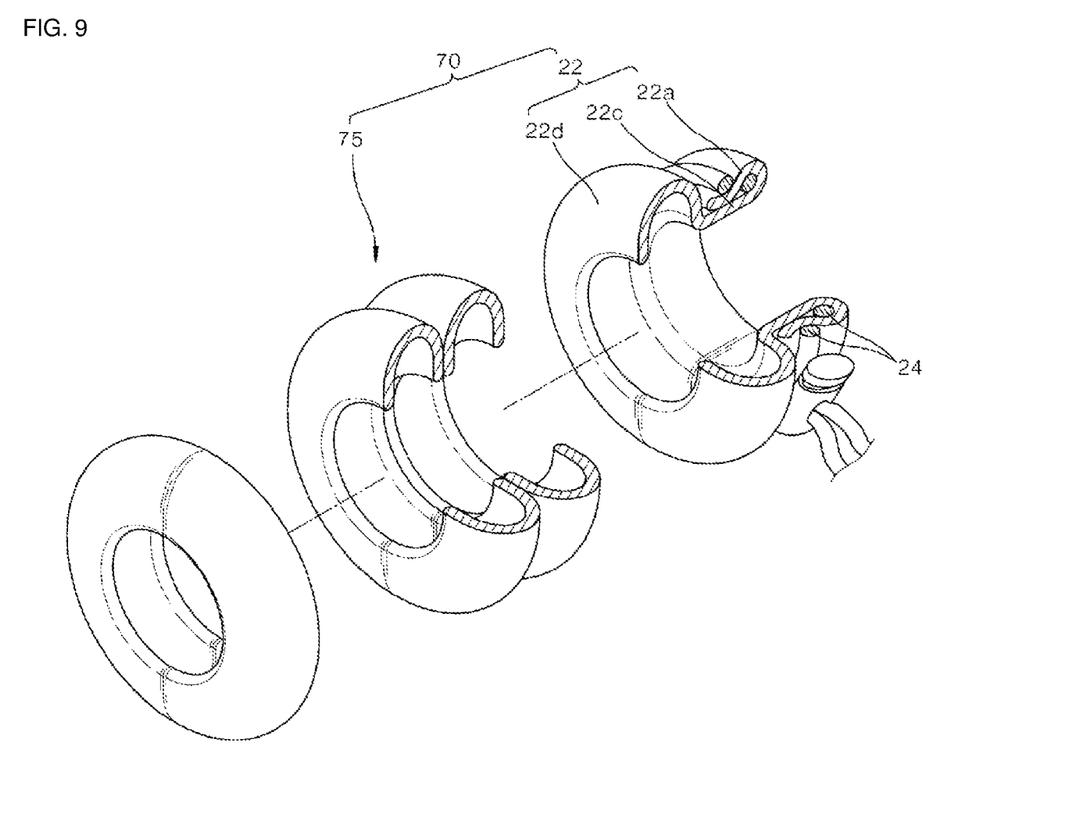
Figure 10:
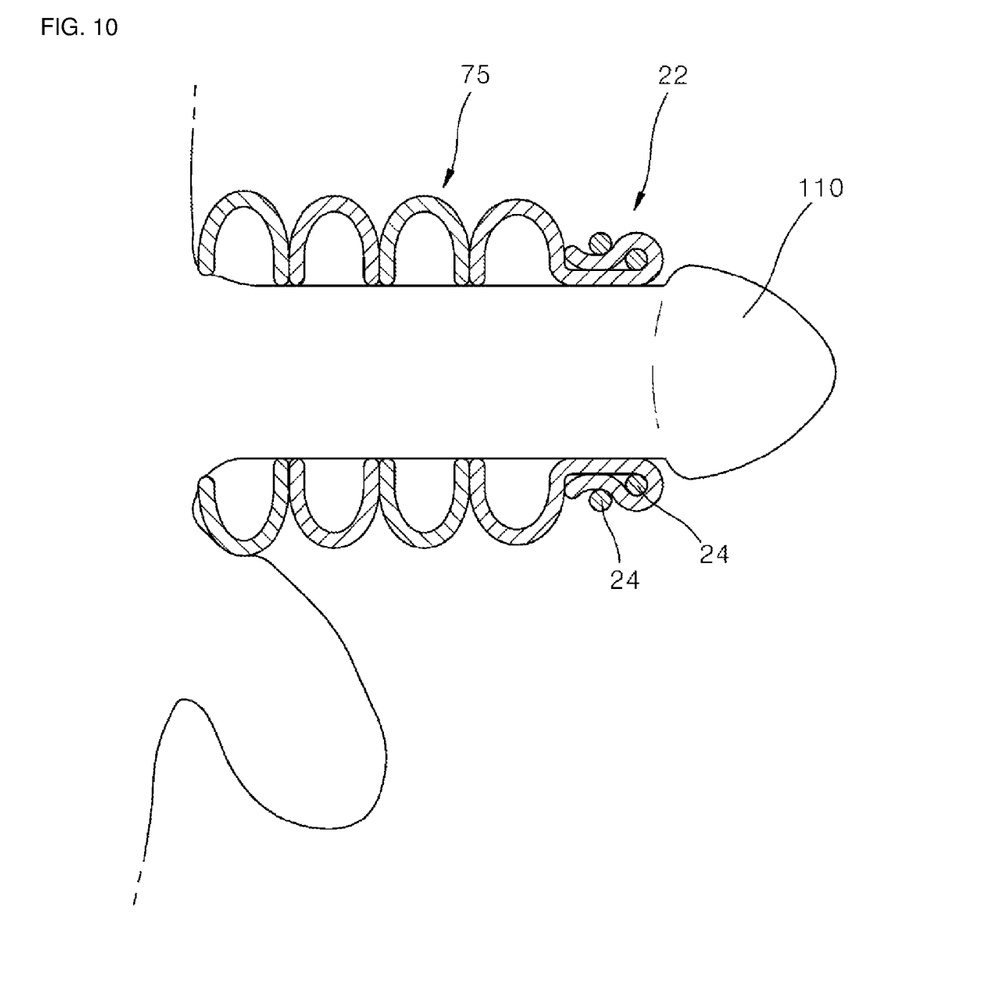
FIG. 10 is a cross-sectional view of the male penis extending and correcting device illustrated in FIG. 9.

Meanwhile, as illustrated in FIGS. 8 to 10, another embodiment of the main body is illustrated. In the embodiment, the same reference numerals as in the embodiment denote the same elements.

The main body 70 may include a traction part 22, and a plurality of elastic support rings 75. The traction part 22 may have a structure that is the same as the structure of the above-described traction part 22. The traction part 22 includes a traction main body 22d having a relatively large diameter, a band winding part 22c extending from the traction main body 22d, and a bending part 22a bent to the rear side, on the outside. A fixing/coupling band 24 may be installed for fixing while the band is not wound may be installed in the band winding part 22c. A fixing/coupling band 24 that is installed in the band winding part 22c or is bent to cover the band winding part 22c may be installed in the bending part 22a. The band 30 may be wound on the traction part 22 as in the embodiment, and the traction part 22 may be pulled by the traction unit.

The elastic support ring 75 may have a hollow portion 22a and have a tire shape, the interior of which is empty, and the present invention is not limited thereto and may be a doughnut-shaped tube. When the elastic support ring 75 is a tube, air may be filled in the interior of the tube. The elastic support rings 75 may be formed of silicon, and it is preferable that they have a thickness that may provide a sufficient elastic force such that a restoring force may be provided when they are compressed in the widthwise direction thereof.

Hereinafter, an operation of the above-described male penis jelq exercise device according to the present invention will be described.

In order to provide a pulling force for treatment of the small size of the penis or massage the penis for active erection by using the male penis jelq exercise device 10 according to the present invention, as illustrated in FIGS. 1 to 6 and 11, the penis 100 is inserted into the hollow portion of the main body 20. Then, it is preferable that the traction part 22 of the main body 20 is located on the rear side that is adjacent to the glans 110.

In this state, the band 30 is wound on the outer peripheral surface of the traction part 22. In this way, opposite ends of the band 30 become thicker and maintain a winding state in which the central portion of the band 30 is recessed. The holding force of the penis 100 may be adjusted by adjusting the winding force of the band 30 having an elastic force when the band 30 is wound on the band winding part 22c of the traction part 22. That is, when the winding force of the band 30 becomes higher, the holding force becomes higher, and when the winding force of the band 30 becomes lower, the holding force may become lower.

The band 30 is prevented from being released as an end of the main body 20 is bent outwards such that the band 30 is surrounded by the bending part 22a in a state in which the band 30 is wound (see FIG. 2).

In this mounting state, because the main body 20 is formed of silicon, the attachment force with the penis 100 becomes relatively higher so that sliding does not occur, and the holding force may be added or subtracted by the band 30. In particular, the wound band 30 is prevented from being released because it is surrounded by the banding part 22a.

It is preferable that a portion, at which the traction part 22 is installed, is a middle portion of the penis 100 or a side that is adjacent to the glans part 110, that is, a two thirds point of the penis. It is preferable that the traction part 22 is located in the skin of the phimosis penis 100, and in this case, the skin is pushed and caught by the glans part and the penis 100 is stopped. In particular, the traction part 22 according to the present invention is tied by using the band 30 of a relatively large width and thus the pains may be minimized.

Further, the testicle 120 is inserted into the testicle ring 27a so that the testicle 120 is prevented from being separated from the groin and the main body 20 is fixed to the penis as well.

Figure 11:
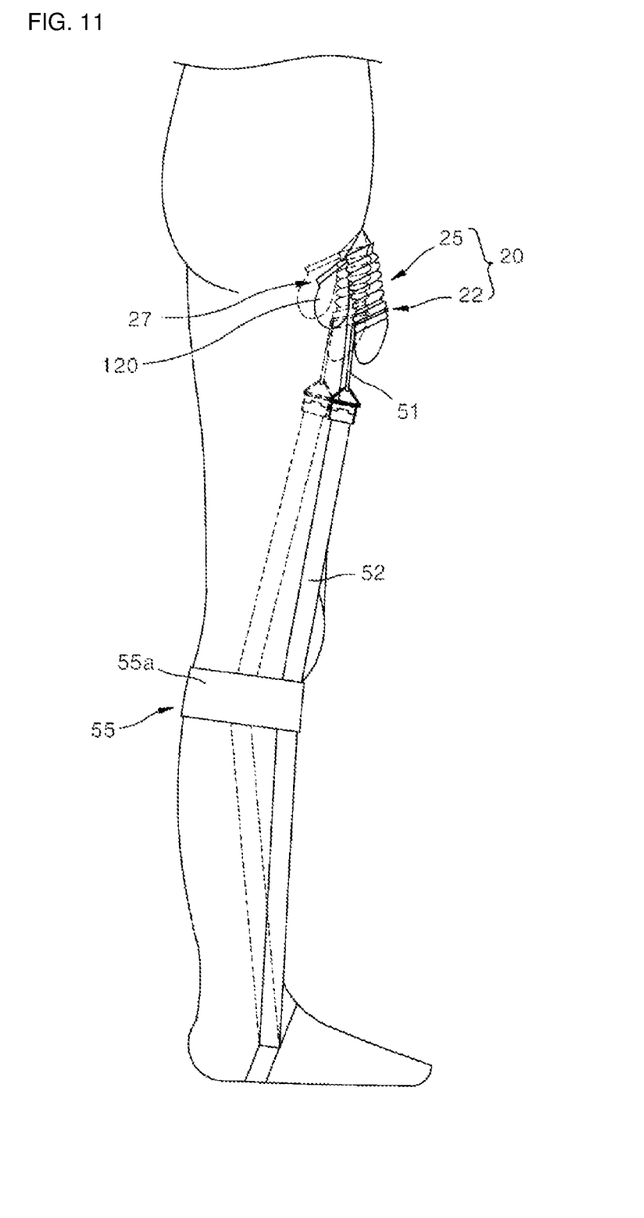
FIG. 11 is a view of an in-use state of the male penis extending and correcting device according to the present invention.

In this way, if the main body 20 is completely installed, as illustrated in FIG. 11, the fastening part 55 of the traction unit 50 is mounted to the thigh of the leg. Further, the penis is made to be pulled by the elastic force of the elastic band part 52 by hanging the coupling part 51 connected to the elastic band part 52 on a coupling/insertion groove 20a of the traction part 22. An auxiliary ring part 57a of an end of the auxiliary elastic band part 57 connected to the fastening part 55 is fitted with the foot so that the fastening part 55 is prevented from moving upwards when the user walks.

In this process, because the main body 20 is formed of elastic silicon or rubber and is bent by the bending part 22b, the main body 20 can be prevented from being separated from the penis even when the penis is relatively small or the glans is small.

In this way, if the coupling to the penis is completed, a pulling force is generated by the elastic band part 52 connected to the fastening part 55. If the user walks in the state, because the elastic band part 52 is periodically prolonged and contracted according to the steps, the variable pulling force may be consistently provided to the penis. In particular, because the elastic traction part 25 is installed in the main body 20, the glans is consistently pushed forwards by the elastic traction part 25 so that a pulling force is provided. Accordingly, in a state in which the user does not walk, the pulling force is consistently applied to the penis 100. The operation of the pulling force may prolong the penis 100.

In this way, in the process of applying a tensile force to the penis 100, a fastening force is generated at a short moment because the coupling part 51 has a loop shape and the ring is released if the coupling part 51 is pulled and if the pulling force disappears so that the coupling part 51 repeatedly fastened and released, which activates circulation of blood.

In particular, the main body 20, into which the penis 100 is inserted, may be located from a point between the groins to a point between the two legs by locating the elastic band part 52 connected to the fastening part 55 between the legs or on the rear side of the legs. In this case, if the user walks, the two legs rub the main body 20 so that the penis is massaged and the circulation of blood can be activated even when the penis is tied. Further, because an effect of periodically massaging the penis 100 is maximized, the distribution of the male hormone can be expedited. Because the testicle is also located between the two legs in the process in which the frictions are applied to the penis, the penis is rubbed and messaged by the two legs, and the discharge of the male hormone is further activated and thus a sensitive feeling portion can become relatively dull.

In particular, the penis 100 is prolonged downwards by the traction part 22, the interference can be minimized when the user walks or works, and the mounting of the device cannot be visually identified from the outside. Further, in the mounting state, because the traction part 22 can be easily coupled and separated by using the coupling part 51, that is, the loop-shaped coupling part, the tensile force can be easily adjusted.

Meanwhile, as illustrated in FIGS. 8 to 10, when the main body 20 includes the traction part 22 and the plurality of elastic support rings 75, the traction part 22 is fixed to an end of the penis 100, that is, a side that is adjacent to the glans part 110 in a state in which the elastic support rings 75 are fitted with the penis and is compressed. In this way, the traction part 22 prolongs the penis 100 while being elastically biased forwards by the elastic support ring 75.

As described above, the male penis jelq exercise device according to the present invention can provide a consistent and variable pulling force to the penis, applying a consistent stimulus to the penis, and can basically prevent pains from being applied to a portion coupled to the coupling part for pulling or circulation of blood from being restrained. In particular, the secreted male hormone can be expedited by applying a periodic stimulus to the penis.

Although one embodiment has been described above with reference to the accompanying drawings, it should be understood that this embodiment is given by way of illustration only, and that various modifications, variations, and alterations can be made without departing from the spirit and scope of the present invention. Hence, the true technical scope of the present invention will be determined by the technical spirit of the claims.

The invention claimed is:
1. A male penis jelq exercise device comprising:
a main body including a traction part having a hollow portion configured to be fitted with a penis, and configured to hold and pull a side thereof, which is adjacent to a glans, and an elastic traction part extending from the traction part to a body side of a penis shaft and configured to contact a human body while configured to surround the penis, and configured to provide a traction force for moving the glans forwards; and
a traction unit including a fastening part configured to be coupled to a leg or the human body, a coupling part caught by the traction part of the main body and formed as a loop, and an elastic band part connecting the coupling part and the fastening part and configured to provide an elastic force for pulling the penis, wherein the traction part includes a band, of which a thickness on at least one lengthwise side is larger than a thickness of an inner side thereof such that the band provides a holding force by using a winding force, and an annular coupling/insertion groove, to which the coupling part is coupled, is formed by bending an end of the main body rearwards such that the end of the main body surrounds the band.

2. The male penis jelq exercise device of claim 1, wherein the main body is formed of silicon having elasticity, and the elastic traction part has a bellow shape to move the traction part of the main body to a front side.

3. The male penis jelq exercise device of claim 2, wherein the elastic traction part further includes an elastic core member for elastically deforming the elastic traction part in a lengthwise direction thereof.

4. The male penis jelq exercise device of claim 1, wherein a testicle ring configured to separate a testicle from a groin while surrounding the testicle and provide a pressure to the testicle is further provided at a rear end of the elastic traction part corresponding to a rear end of the main body.

\* \* \* \* \*